(12) United States Patent
Bhide et al.

(10) Patent No.: US 6,933,386 B2
(45) Date of Patent: Aug. 23, 2005

(54) PROCESS FOR PREPARING CERTAIN PYRROLOTRIAZINE COMPOUNDS

(75) Inventors: Rajeev S. Bhide, Princeton Junction, NJ (US); Junying Fan, Monmouth Junction, NJ (US); Luca Parlanti, Princeton, NJ (US); Stephanie Barbosa, Lambertville, NJ (US); Ligang Qian, Hopewell, NJ (US); Zhen-Wei Cai, Belle Mead, NJ (US); Francis S. Gibson, Pennington, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/622,280

(22) Filed: Jul. 18, 2003

(65) Prior Publication Data

US 2004/0077858 A1 Apr. 22, 2004

Related U.S. Application Data

(60) Provisional application No. 60/397,256, filed on Jul. 19, 2002, and provisional application No. 60/447,213, filed on Feb. 13, 2003.

(51) Int. Cl.$^7$ .............................................. C07D 487/04
(52) U.S. Cl. ...................................... 544/183; 548/452
(58) Field of Search ........................... 544/183; 548/452

(56) References Cited

U.S. PATENT DOCUMENTS

2003/0069244 A1   4/2003   Leftheris et al.

FOREIGN PATENT DOCUMENTS

| WO | WO 00/71129 | 11/2000 |
|----|-------------|---------|
| WO | WO02/40486  | 5/2002  |

OTHER PUBLICATIONS

Wolft Manfred E. "Burger's Medicinal Chemistry, 5ed, Part 1", John Wiley & Sons, 1995, pp. 975–977.*
Banker, G.S. et al., "Modern Pharmaceutices, 3ed.", Marcel Dekker, New York, 1996, p. 596.*
West, Anthony R., Solid State Chemistry and its Applications, Wiley, New York, 1988. pp. 358 & 365.*
Fan et al., Trend Pharmacol. Sci. vol. 16, pp. 57–66 (1995).
Folkman, Nature Medicine, vol. 1, pp. 27–31 (1995).
Cullinan–Bove et al., Endocrinology, vol. 133, pp. 829–837 (1993).
Senger et al., Cancer and Metastasis Reviews, vol. 12, pp. 303–324 (1993).
DeVries et al., Science, vol. 255, pp. 989–991 (1992).
Terman et al., Biochem. Biophys. Res. Comm., vol. 187, pp. 1579–1586 (1992).
Jakeman et al., Endocrinology, vol. 133, pp. 848–859 (1993).
Kolch et al., Breast Cancer Research and Treatment, vol. 36, pp. 139–155 (1995).
Connolly et al., J. Biol. Chem., vol. 264, pp. 20017–20024 (1989).

* cited by examiner

*Primary Examiner*—Venkataraman Balasubramanian
(74) *Attorney, Agent, or Firm*—Elliott Korsen

(57) ABSTRACT

The present invention relates to a process for preparing certain pyrrolotriazine compounds of the formula

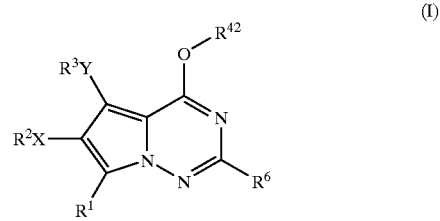

(I)

and pharmaceutically acceptable salts thereof.

The formula I compounds inhibit the tyrosine kinase activity of growth factor receptors such as VEGFR-2 and FGFR-1, thereby making them useful as anti-cancer agents. The formula I compounds are also useful for the treatment of other diseases associated with signal transduction pathways operating through growth factor receptors.

10 Claims, No Drawings

PROCESS FOR PREPARING CERTAIN PYRROLOTRIAZINE COMPOUNDS

This application claims the priority benefit of U.S. Provisional Application No. 60/397,256 filed Jul. 19, 2002 and No. 60/447,213 filed Feb. 13, 2003, the disclosures of which are incorporated herein by reference in their entirety.

FIELD OF THE INVENTION

This invention relates to novel, improved processes for the preparation of certain pyrrolotriazine compounds that inhibit the tyrosine kinase activity of growth factor receptors such as VEGFR-2, and FGFR-1, thereby making them useful as anti-cancer agents. The compounds prepared by the processes of the invention are also useful in the treatment of diseases, other than cancer, which are associated with signal transduction pathways operating through growth factors and anti-angiogenesis receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in EC activation. Disruption of these pathways should inhibit endothelial cell activation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

Compounds that can benefit from the processes of the invention include those in the priority applications as well as compounds disclosed in WO 00/71129, which are hereby incorporated by reference in their entirety.

SUMMARY OF THE INVENTION

The present invention provides a process for the preparation of certain pyrrolotriazine compounds. The process of the invention provides a useful, convenient and improved preparation of pyrrolotriazine derivatives containing a hydroxyl group attached directly to the pyrrolotriazine ring.

The process of the invention comprises, in one embodiment, the steps of reacting a chloro-substituted pyrrolotriazine with an oxide anion to form an ether; converting the ester to a benzylic alcohol, oxidatively rearranging the alcohol to form a phenol The hydroxyl compound is subsequently alkylated with an electrophilic agent to afford a phenoxy substituted compound which is hydrolyzed to afford an amide. This is converted to the final compound by first forming a chloroimidate and reacting this with an alkylating agent such as hydroxy fluoroindole in the presence of a base in a polar solvent to afford the final compound.

In a second embodiment, the invention provides a process for preparing the fluoroindole portion of the compounds using a novel and improved process that is amenable to large scale preparations and provides fluoroindole derivatives of high quality. In addition, fluoroindole derivatives prepared using the process described herein are stable solids that are easy to isolate and have long term stability, giving products of higher quality than fluoroindole derivatives prepared using alternative methods.

DETAILED DESCRIPTION OF THE INVENTION

The present invention provides a process for the preparation of certain pyrrolotriazine compounds of the formula

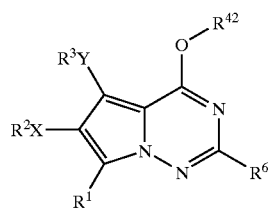

(I)

their enantiomers, diastereomers, and pharmaceutically acceptable salts, prodrugs and solvates thereof which inhibit the tyrosine kinase activity of growth factor receptors such as VEGFR-2. In formula I and throughout the specification, the above symbols are defined as follows:

X and Y are independently selected from O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, $NR^{16}SO_2NR^{17}$, $SO_2NR^{18}$, $CONR^{19}$, halogen, nitro, cyano, or X or Y are absent;

$R^1$ is hydrogen;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heteroaryl, substituted heteroaryl, heterocycloalkyl or substituted heterocycloalkyl; with the proviso that when X is halo, nitro or cyano, $R^2$ is absent, and, when Y is halo, nitro or cyano, $R^3$ is absent;

$R^6$ is H;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are independently selected from the group consisting of hydrogen, alkyl, substituted alkyl, aryl, substituted aryl, heteroaryl, substituted heteroaryl, heterocyclo, or substituted heterocyclo;

$R^{42}$ is

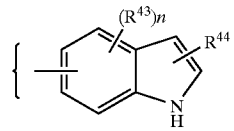

$(R^{43})_n$ wherein n equals 0, 1 or 2 and each $R^{43}$ is independently selected from the group consisting of hydrogen, fluorine, chlorine and methyl; and $R^{44}$ is methyl, or hydrogen, with the further provisos that:
a. $R^2$ may not be hydrogen if X is SO, $SO_2$, $NR^{13}CO_2$, or $NR^{14}SO_2$; and
b. $R^3$ may not be hydrogen if Y is SO, $SO_2$, $NR^{13}CO_2$, or $NR^{14}SO_2$.

The process of the invention comprises, in one embodiment, the steps of a) converting a compound of the formula

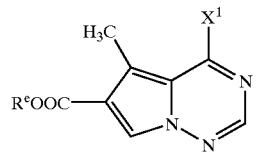

where $R^e$ is lower alkyl or aryl and $X^1$ is halogen, to a compound 1 of the formula

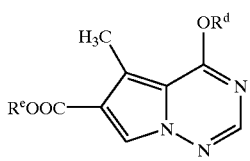

1 where $R^d$ is lower alkyl, aryl, substituted aryl, heteroaryl or substituted heteroaryl by treatment with a phenoxide or alkoxide, b) alkylating Compound 1 to afford Compound 2 of the formula

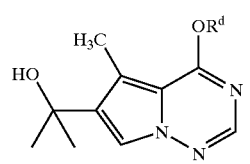

2 c) treating compound 2 with a peroxide in the presence of a Lewis acid to afford compound 3 of the formula

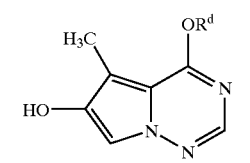

3 d) alkylating the phenol group in compound 3 to afford Compound 4 of the formula

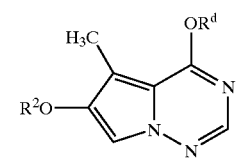

4 where $R^2$ is benzyl or substituted benzyl, e) hydrolyzing Compound 4 to afford Compound 5 of the formula

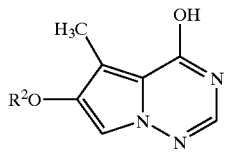

where $R^2$ is benzyl or substituted benzyl, and f) converting Compound 5 to Compound 6 of the formula

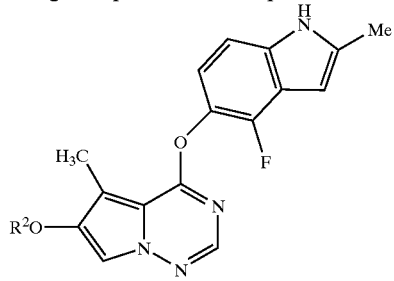

by first converting compound 5 to a chloroimidate and subsequently alkylating the chloroimidate to afford Compound 6 wherein $R^2$ is benzyl. The deprotection of phenol is accomplished by treatment with hydrogen donor in presence of a catalyst to afford compound 6 where $R^2$ is hydrogen.

In a second embodiment of the invention, the starting compound of the formula

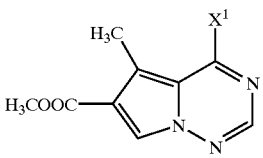

where $X_1$ is halogen;
is reacted with a nucleophile to afford Compound 8 of the formula

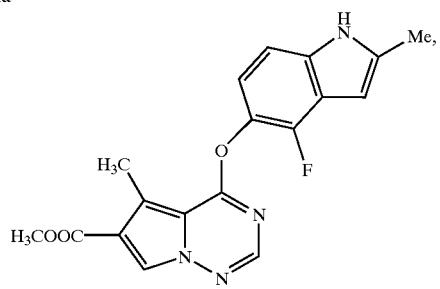

which is treated with an alkylating agent at low temperature, to afford Compound 9 of the formula

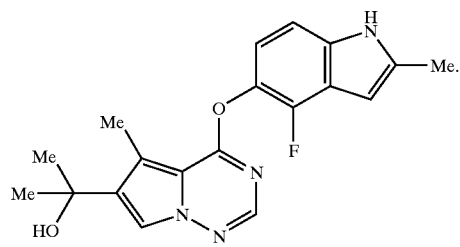

Compound 9 is then treated with a peroxide in the presence of a Lewis acid to afford Compound 10 of the formula

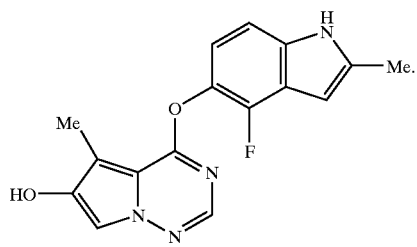

In a further embodiment of the invention, the fluoroindole piece can be prepared as follows:

a) reacting a fluorinated compound of the formula

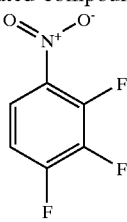

with a nucleophile to afford Compound 11 of the formula

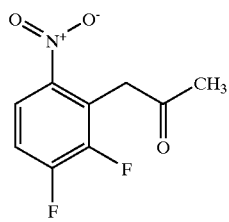

b) reacting Compound 11 with an alkoxy anion to afford Compound 12 of the formula

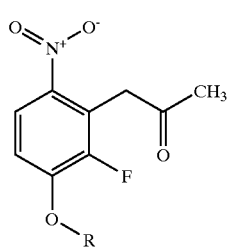

wherein R is a protecting group, c) deprotecting the alkoxy group by treatments with deprotecting reagents to afford Compound 13 of the formula

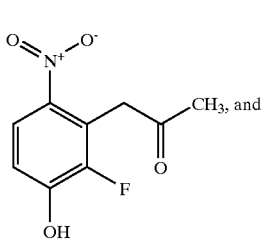

d) cyclizing Compound 13 under reducing conditions to afford Compound 14 of the formula

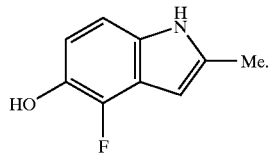

In a preferred embodiment, step 1 of scheme 1 involved the conversion of the compound to an ether by treatment with a nucleophile such as a phenoxide or alkoxide anion. Preferably, the alkoxide anion is a methoxide or ethoxide anion.

Preferred alkylating agents in step 2 of scheme 1 include an alkyl magnesium halide, i.e., methyl magnesium bromide or methyl magnesium chloride at low temperature from about −25° C. to about 25° C.

Compound 2 in step 3 is preferably treated with an peroxide such as hydrogen peroxide or sodium perborate in the presence of a Lewis acid such as boron trifluoride in an organic solvent such as dichloromethane (DCM) to afford compound 3. Compound 3 is alkylated with an electrophilic agent such as benzyl bromide or benzyl chloride in the presence of a base such as NaH at a temperature from about 0° C. to about 100° C.

Compound 4 is hydrolyzed by treatment with an acid, preferably aqueous HCl at an elevated temperature to afford Compound 5. Compound 5 is finally converted to Compound 6 through the chloroimidate which is subsequently alkylated, preferably with hydroxy fluoroindole, in the presence of a base such as potassium carbonate or sodium hydride in a polar solvent such as dimethylformamide (DMF) or toluene, preferably DMF. The benzylic deprotection is achived by treatment with an hydrogen source such as ammonium formate in the presence of a catalyst such as Palladium on carbon.

Preferred conditions for the second embodiment include in step 1, the use of a nucleophile such as fluoroindole in the presence of a base such as potassium carbonate or sodium hydride to treat Compound 7 to afford Compound 8. This reaction takes place, preferably, in a polar solvent such as DMF. Step 2 involves treating Compound 8 with an alkylating agent, such as an alkyl magnesium halide, i.e, methyl magnesium bromide or methyl magnesium chloride at low temperature from about −25° C. to about 25° C. In a preferred embodiment, Step 3 involves treating Compound 9 with a peroxide such as hydrogen peroxide or sodium perborate in the presence of a Lewis acid such as boron trifluoride at a temperature from about −25° C. to about 25° C. to afford Compound 10.

In the preparation of the indole side chain, the starting fluorinated compound, in this case, trifluoronitrobenzene, can be reacted with a nucleophile such as ethyl acetoacetate or tet-butylacetoacetate, which is followed by decarboxylation of the ester group in the presence of an acid or base, preferably an aqueous acid. In step 2, Compound 11 is reacted with an alkoxy anion such as sodium methoxide or methanol in the presence of a base such as potassium carbonate or the sodium salt of benzyl alcohol to afford Compound 12. The alkoxy or benzyloxy group is then deprotected by treatment with a deprotecting reagent such as pyridinium chloride or hydrogen bromide in acetic acid to afford Compound 13. In the final step, Compound 13 is cyclized under reducing conditions preferably using reduction agents such as sodium dithionate or palladium on carbon in the presence of a hydrogen source to afford the desired indole compounds.

The invention also provides a pharmaceutical composition comprising a compound of formula I or II and a pharmaceutically acceptable carrier.

The invention also provides a pharmaceutical composition comprising a compound of formula I or II in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; gosereline acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cis-platin; carboplatin; nitrogen mustard; melphalan; chlorambucil; busulphan; cyclophosphamide; ifosfamide nitrosoureas; thiotepa; vincristine; Taxol® (paclitaxel); Taxotere® (docetaxel); epothilone analogs; discodermolide analogs; eleutherobin analogs; etoposide; teniposide; amsacrine; topotecan; flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I.

Additionally, there is disclosed a method of inhibiting tyrosine kinase activity of at least one growth factor receptor such as which comprises administering to a mammalian species in need thereof, a therapeutically effective amount of a compound of formula I or II. In a preferred embodiment said growth factor receptor is selected from the group consisting of VEGFR-2 and FGFR-1.

Finally, there is disclosed a method for treating a proliferative disease, comprising administering to a mammalian species in need thereof, a therapeutically effective amount of a compound of formula I. In a preferred embodiment the proliferative disease is cancer.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, indole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzimidazolyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

Thus according to a further aspect of the invention, there is provided the use of a compound of formula I, or a pharmaceutically acceptable salt thereof in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of a compound of formula I or a pharmaceutically acceptable salt thereof as defined herein before.

The compounds described herein also inhibit other receptor tyrosine kinases including HER1 and HER2 and are therefore useful in the treatment of proliferative disorders such as psoriasis and cancer. The HER1 receptor kinase has been shown to be expressed and activated in many solid tumors including non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. The ability of these compounds to inhibit HER1 further adds to their use as antiangiogenic agents. See the following documents and references cited therein: Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000).

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates like methotrexate, fluoropyrimidines like 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids such as vincristine and taxoids such as Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan); cell cycle inhibitors (for example, flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors can act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2 and FGFR-1.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may also be administered as suspensions using carriers appropriate to this mode of administration. The compounds may be administered in a dosage range of about 0.05 to 300 mg/kg/day, preferably less than 200 mg/kg/day, in a single dose or in 2 to 4 divided doses.

METHODS OF PREPARATIONS

Certain compounds of formula I may be prepared according to the following schemes and the knowledge of one skilled in the art.

All temperatures are in degrees Celsius (° C.) unless otherwise indicated. Preparative Reverse Phase (RP) HPLC purifications were done on C18 reverse phase (RP) columns YMC S5 ODS columns eluting with 90% aqueous methanol containing 0.1% TFA as buffer solution and monitoring at 220 nm. For analytical HPLC 0.2% phosphoric acid was used instead of TFA. All of the synthesized compounds were characterized by at least proton NMR and LC/MS. During work up of reactions, the organic extract was dried over magnesium sulfate ($MgSO_4$), unless mentioned otherwise.

The following abbreviations are used for the commonly used reagents. $Et_2O$; diethyl ether, $Na_2SO_4$; sodium sulfate;

HCl; hydrochloric acid, NaOH; sodium hydroxide, NaCl; sodium chloride, Pd/C; palladium on carbon, K₂HPO₄; potassium monohydrogen phosphate, K₂CO₃; potassium carbonate, NaHCO₃; sodium bicarbonate, LiOH; lithium hydroxide, RT; room temperature, TFA; trifluoroacetic acid, h; hour.

Step 1

A compound from PCT Publication WO 0071129 is converted to an ether (etherified) at the 4-position, for example, by treatment with phenoxide or methoxide or ethoxide anion.

Step 2

Compound 1 can then be treated with an alkylating agent such as methyl magnesium bromide or methyl magnesium chloride, at low temperatures to afford compound 2.

Step 3

Compound 2 can then be treated with a peroxide such as hydrogen peroxide or sodium perborate in the presence of a Lewis acid, such as boron trifluoride, at low temperature to afford phenolic compound 3.

Step 4

Alkylation of the phenol group in compound 3 with an electrophilic agent, such as benzyl bromide, in the presence of a base, such as NaH, at from 0° C. to 80° C., affords compound 4.

Step 5

Hydrolysis of compound 4 of this scheme is achieved by treatment with an acid, such as aqueous HCl, at an elevated temperature, to afford compound 5.

Step 6

Compound 5 of this scheme is converted to compound 6 by first converting to chloroimidate as described above followed by alkylation of the resulting chloroimidate with a hydroxy fluoroindole in the presence of a base such as potassium carbonate in a polar solvent such as dimethyl formamide to afford protected compound 6.

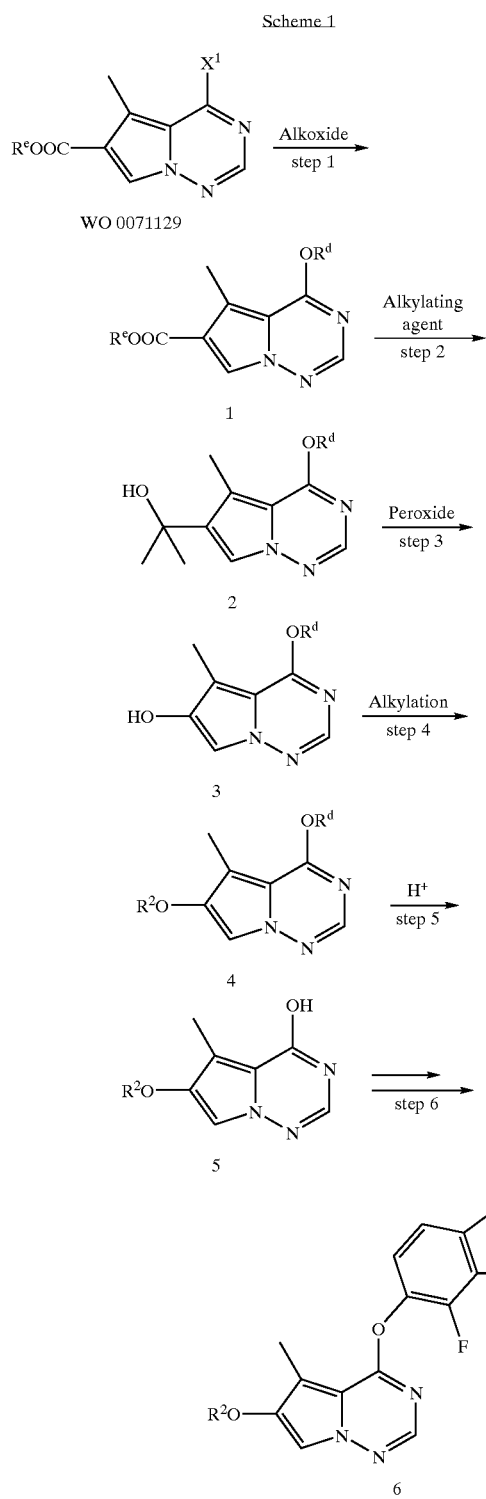

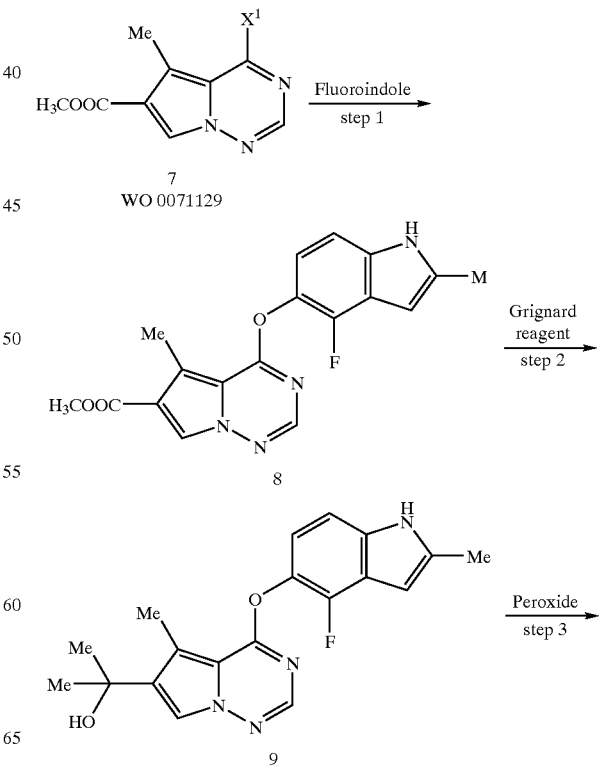

-continued

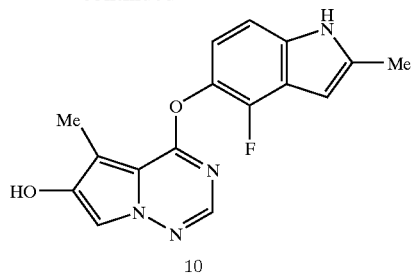

10

-continued

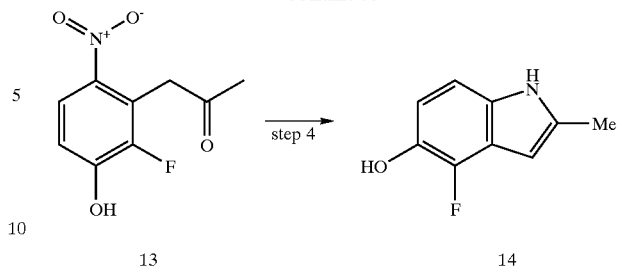

Step 1

A fluorinated compound such as trifluoro nitrobenzene can be reacted with a nucleophile such as ethyl acetoacetate followed by decarboxylation of ester group in the presence of an acid or base to give compound 11.

Step 2

Compound 11 can then be reacted with an alkoxy anion such as sodium methoxide or sodium salt of benzyl alcohol to give compound 12.

Step 3

Deprotection of the alkoxy group of Compound 12 of this scheme then can be accomplished by treatment with reagents like pyridinium chloride or hydrogen bromide in acetic acid to give compound 13.

Step 4

Compound 13 then could be cyclized under reducing conditions such as sodium dithionite or palladium on carbon in the presence of hydrogen to give the indole derivatives of the formula 14.

Compound 12 could directly be converted to compound 14 by treatment with palladium on carbon in the presence of hydrogen source such as ammonium formate.

Step 1

A compound from PCT Publication WO 0071129, wherein $X_1$ is halogen, such as chlorine, can be treated with a nucleophile such as fluoroindole in the presence of a base such as potassium carbonate in a polar solvent such as dimethyl formamide to afford compound 8.

Step 2

Compound 8 can then be treated with an alkylating agent such as methyl magnesium bromide or methyl magnesium chloride, at low temperatures to afford compound 9.

Step 3

Compound 9 can then be treated with a peroxide such as hydrogen peroxide or sodium perborate in the presence of a Lewis acid, such as boron trifluoride, at low temperature to afford phenolic compound 10.

Scheme 3

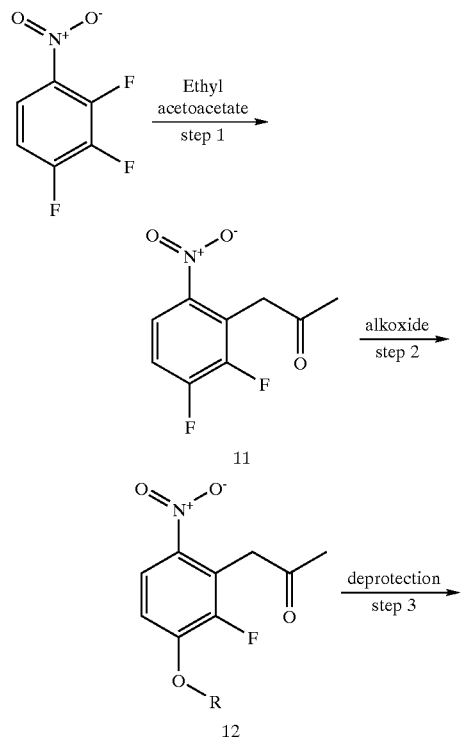

EXAMPLE 1

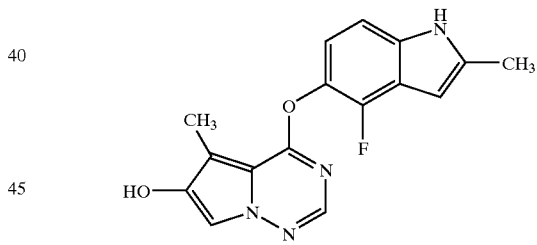

4-(4-Fluoro-2-methyl-1H-indol-5-yloxy)-5-methylpyrrolo[2,1-f][1,2,4]triazin-6-ol A. 4-Chloro-5-methylpyrrolo[2,1-f][1,2,4]triazine-6-carboxylic acid ethyl ester A mixture of 4-hydroxy-5-methylpyrrolo[2,1-f][1,2,4]triazine-6-carboxylic acid ethyl ester (60.0 g, 271.2 mmol, for preparation see WO 0071129), phosphorus oxychloride (30.3 mL, 325.4 mmol) and diisopropylethyl amine (37.7 mL, 217 mmol) in toluene (800 mL) was heated to reflux under argon for 18 h and then cooled to room temperature. The mixture was concentrated on rotovap and the residue was diluted with dichloromethane (1000 mL) and cold sodium bicarbonate solution (300 mL). The resulting mixture was stirred at room temperature for 10 min. The separated organic layer was washed with cold brine (300 mL), dried, and concentrated in vacuo. The crude material was purified by chromatography on silica gel eluting with dichloromethane to provide the desired compound (64.8 g, 99%) as a yellow solid.

B. 4-Ethoxy-5-methylpyrrolo[2,1-f][1,2,4]triazine-6-carboxylic acid ethyl ester To a solution of compound A of this example (23 g, 96 mmol) in tetrahydrofuran (0.6 L) under argon at 0° C. was added sodium ethoxide in ethanol (21% w/w, 43 mL, 115.2 mmol) dropwise over 20 min. The reaction was stirred at 0° C. for 1 hr, diluted with ethyl acetate and washed with ammonium chloride solution and brine. The organic layer was dried, concentrated and the residue was purified by chromatography on silica gel eluting with dichloromethane followed by 50% ethyl acetate in hexanes to provide the desired compound (23.5 g, 98%) as a white solid. LC/MS; $(M+H)^+=250.17$

C. 2-(4-Ethoxy-5-methylpyrrolo[2,1-f][1,2,4]triazin-6-yl)-propan-2-ol

To a solution of compound B of this example in THF (2.5 L) at 0° C. was slowly added methyl magnesium bromide (3M in Et$_2$O, 360 mL, 1.08 mol) with addition funnel. The mixture was allowed to warm to room temperature, whereupon stirring was continued for 4 h. The reaction was quenched by ammonium chloride solution and extracted with ethyl acetate. The organic layer was washed with sodium chloride solution and dried, to afford the desired compound (78 g, 100%) as a yellow solid. LC/MS; $(M+H)^+=236.1$

D. 4-Ethoxy-5-methylpyrrolo[2,1-f][1,2,4]triazin-6-ol

A mixture of hydrogen peroxide (30%, 10.3 mL, 178.5 mmol) and boron trifluoride diethyl etherate(271.4 mL, 2.14 mol) was stirred at 0° C. for 30 min. It was then cooled to −20° C. and a solution of Compound C of this example (30 g, 129.5 mmol) in dichloromethane (1.45 L) at −15° C. was added. The reaction mixture reached −3° C., and then cooled to −40° C. To this mixture was added a saturated solution of sodium sulfite with stirring. The resulting mixture was extracted with ethyl acetate, dried, and concentrated in vacuo to provide Compound D (26 g, 76%). LC/MS; $(M+H)^+=194.2$

E. 6-Benzyloxy-4-ethoxy-5-methylpyrrolo[2,1-f][1,2,4]triazine

A mixture of compound D of this example (1 g, 5.2 mmol), benzyl bromide (0.62 mL, 5.2 mmol) and potassium carbonate (2.1 g, 15.5 mmol) in dimethyl formamide (10 mL) was stirred at room temperature for 12 h. The reaction was diluted with ethyl acetate and washed with water, 10% lithium chloride solution and brine. The organic layer was dried (Na$_2$SO$_4$) and concentrated in vacuo to give Compound E (1 g) as yellow solid which was used without further purification for the next step.

F. 6-Benzyloxy-5-methylpyrrolo[2,1-f][1,2,4]triazin-4-ol

Compound E of this example (90 g, crude) in 1N HCl (600 mL) and ethanol (800 mL) was heated to reflux for 4 h. A solid precipitated which was collected by filtration, washed with a mixed solvent (water/ethanol/methanol=4/4/2) and dried to give a off-white solid, which was washed with dichloromethane to afford Compound F (65 g) as a white solid. LC/MS; $(M+H)^+=256.2$

G. 6-Benzyloxy-4-chloro-5-methylpyrrolo[2,1-f][1,2,4]triazine

A mixture of compound F of this example (10 g, 39.2 mmol), phosphorus oxychloride (4.4 mL, 47.1 mmol) and diisopropylethyl amine (5.5 mL, 31.4 mmol) in toluene (150 mL) was stirred at 85° C. for 2 h and then more phosphorus oxychloride (1.1 mL, 11.8 mmol) was added. After 2 h, additional phosphorus oxychloride (1.1 mL, 11.8 mmol) was added. The reaction mixture was continuously stirred at 85° C. for 1 h and then concentrated. The residue was dissolved in dichloromethane, washed with cold sodium bicarbonate solution, dried, and concentrated in vacuo. The crude material was purified by chromatography on silica gel eluting with dichloromethane to provide Compound G (9.9 g, 93%) as a yellow solid.

H. 6-Benzyloxy-4-(4-fluoro-2-methyl-1H-indol-5-yloxy)-5-methylpyrrolo[2,1f][1,2,4]triazine A solution of 4-fluoro-2-methyl-1H-indol-5-ol (6.47 g, 39.2 mmol, Example 2) in dimethyl formamide (100 mL) was degassed with argon and then cooled to −20° C. Sodium hydride (60% in oil, 1.57 g, 39.2 mmol) was added in one portion. The reaction mixture was allowed to warm to 0° C. with stirring over 30 min, cooled back to −20° C. and a solution of Compound G of this example in dimethyl formamide (100 mL) was added in one portion. The reaction was warmed to room temperature. After 30 min, the mixture was acidified with 1N HCl (200 mL), diluted with ethyl acetate (1.8 L), and washed with a 10% lithium chloride solution (0.4 L×2), 1N NaOH solution (0.3 L×2), buffer (pH=2,200 mL), and NaCl solution (0.4 L). The organic layer was dried, and concentrated in vacuo to provide Compound H (15 g, 95%) as a tan solid. LC/MS; $(M+H)^+=403.1$

I. 4-(4-Fluoro-2-methyl-1H-indol-5-yloxy)-5-methylpyrrolo[2,1-f][1,2,4]triazin-6-ol A mixture of Compound H of this example (15 g, 37.3 mmol), ammonium formate (12 g, 190 mmol) and Pd/C (10%, 1.5 g) in dimethyl formamide (100 mL) was stirred at room temperature for 2 h. The mixture was filtered through Celite® and the filtrate was diluted with ethyl acetate and washed successively with 10% lithium chloride solution (2×), 5% sodium bicarbonate solution (2×) and brine. The organic layer was dried (Na$_2$SO$_4$), and concentrated in vacuo to gave a light-brown solid, which was washed with dichloromethane to afford the title compound (7.8 g, 64%) as an off-white solid. MS: $[M+H]^+=313.2$. $^1$HNMR (CDCl$_3$): δ 2.44 (s, 3H), 2.51(s, 3H), 6.31 (s, 1H), 6.95 (dd, 1H), 7.07 (d, 1H, J=8.8 Hz), 7.38 (s, 1H), 7.78 (s, 1H).

Example 1 can also be prepared by the alternate route described below.

A-1. 4-Chloro-5-methyl-pyrrolo[2,1-f][1,2,4]triazine-6-carboxylic acid ethyl ester A 10 L reactor was charged with 4-hydroxy-5-methyl-pyrrolo[2,1-f][1,2,4]triazine-6-carboxylic acid ethyl ester (155.1 g, 0.7 mol) and toluene (2.7 L). Phosphorous oxychloride (128.8 g, 78 mL, 0.84 mol) was then added followed by the addition of diisopropylethylamine (94.2 g, 127 mL, 0.7 mol). The reaction mixture was stirred for 5 min at room temperature and then heated at reflux for 20 h. HPLC analysis indicated complete disappearance of starting material. The reaction mixture was then cooled to 0° C. and cold K$_2$HPO$_4$ solution (527 g in 2.4 L of water) was added at a rate to maintain the internal temperature of the reaction mixture below 5° C. The final pH of the mixture was 8. The mixture was then stirred at between 0° C. to 5° C. for 20 min and then at room temperature for 1 h. The organic phase was separated and washed with $K_2HPO_4$ solution (85 g in 405 mL of water) and water (345 mL) and then filtered and concentrated in vacuo until yellow solids began to precipitate. Dimethyl formamide (1 L) was added and the remaining toluene was removed in vacuo (bath temperature=38° C., pressure=9 Torr). After concentration, approximately 4% toluene was observable by HPLC.

J. 4-(4-Fluoro-2-methyl-1H-indol-5-yloxy)-5-methylpyrrolo[2,1-f][1,2,4]triazine-6-carboxylic acid ethyl ester The residue from previous step A-1 was transferred to a 10 L reactor and dimethyl formamide (1.1 L) was added followed by $K_2CO_3$ (276 g, 2.1 mol) and 4-fluoro-2-methyl-1H-indol-5ol (109.5 g, 0.7 mol). The reaction mixture was stirred at ambient temperature for 16 h and then cooled to 0° C. Water (2.0 L) and ethyl acetate (2 L) were added at a rate so as to maintain the internal temperature below 20° C. The phases were then separated and the aqueous phase was extracted with ethyl acetate (2 L). The combined organic extracts were then washed with water (2 L), 10% aqueous LiCl (2 L) and water (2 L). Toluene (1 L) was then added and the organic extracts were concentrated in vacuo. Additional toluene (500 mL) was added and the mixture was reconcentrated in vacuo. LC/MS; $(M+H)^+=369.4$. $^1$HNMR ($CDCl_3$): δ 1.41 (t, 3H, J=7.15 Hz), 2.45 (s, 3H), 2.87 (s, 3H), 4.39 (q, 2H, J=7.15 Hz), 6.34 (s, 1H), 6.98 (dd, 1H), 7.08 (d, 1H, J=8.25 Hz), 7.90 (s, 1H), 8.15 (s, 1H).

K. 2-[4-(4-Fluoro-2-methyl-1H-indol-5-yloxy)-5-methyl-pyrrolo[2,1-f][1,2,4]triazin-6-yl]-propan-2-ol The residue from the previous step (step J) was transferred to a 10 L reactor and enough toluene was added to provide a total reaction volume of 1.1 L. THF (1.1 L) was then added followed by the addition of LiCl (140 g) and the reaction mixture was cooled to 0° C. Methyl magnesium bromide [1.4 M in toluene, THF (75:25), 2.1 L, 2.8 mol] was then added at a rate so as to maintain an internal temperature below 5° C. Total addition time was approximately 2 h. The reaction mixture was stirred at 0° C. for an additional 2 h and then warmed to 15° C. over 3 h, at which time 5% of the starting material was still observable by HPLC. The reaction mixture was then recooled to 5° C. and an additional 100 mL of methylmagnesium bromide was added and the mixture was stirred for an additional 1.5 h. Ethyl acetate (1.5 L and a solution of 15% $NH_4Cl$ (3.2 L) and) were then added so as maintain an internal temperature below 5° C. The layers were then separated and the aqueous phase was extracted with ethyl acetate (2 L). The combined organic layers were washed with 15% $NH_4Cl$ (2×2 L) and water (2×2 L) and then concentrated in vacuo to afford the desired product as an amorphous yellow solid. The crude product was dissolved in dichloromethane (5 L) using a water bath (T=37° C.) to aid dissolution. The solution was then passed through a short pad of silica gel (400 g) and the pad was washed with dichloromethane (7 L) and 5% ethyl acetate/dichloromethane (1.2 L). The filtrate was evaporated to yield an off-white solid to which ethyl acetate (1.2 L) was added. The resulting slurry was transferred to a 10 L reactor and a clear solution was obtained after stirring for 2 h at 50° C. The solution was then cooled to ambient temperature and a white solid precipitated. Heptane (2.6 L) was then added and the mixture was stirred at room temperature for 20 h. The resulting solids were filtered, washed with heptane (1 L) and dried under reduced pressure at 50° C. for 24 h. 2-[4-(4-Fluoro-2-methyl-1H-indol-5-yloxy)-5-methylpyrrolo[2,1-f][1,2,4]triazin-6-yl]-propan-2-ol was obtained as a white solid (186 g, 75% over 3 steps). LC/MS; $(M+H)^+=355.4$

I-1. 4-(4-Fluoro-2-methyl-1H-indol-5-yloxy)-5-methylpyrrolo[2,1-f][1,2,4]triazin-6-ol To a solution of $BF_3.OEt_2$ (120 mL, 0.948 mol) in dichloromethane (200 mL) at 0° C. was added $H_2O_2$ (50% aqueous solution, 4.6 mL, 0.079 mol). The reaction mixture was stirred at 0° C. for 30 min and then cooled to −20° C. In a separate flask, 2-[4-(4-fluoro-2-methyl-1H-indol-5-yloxy)-5-methylpyrrolo[2,1-f][1,2,4]triazin-6-yl]-propan-2-ol from previous step (20 g, 0.0564 mol) was dissolved in dichloromethane (400 mL) using indirect heat to achieve complete dissolution. This solution was then added rapidly via canula (addition time=20 min) to the peroxide solution. The reaction temperature during the addition was between −15° C. and −25° C. After the addition was complete, the reaction temperature was raised to −15° C. and maintained at that temperature for an additional 40 min. The reaction mixture was quenched by the addition of $Na_2SO_3$ (200 mL, 20% aqueous solution) and ethanolamine (33% aqueous solution, 300 mL). Both reagents were added at a rate so as to maintain the internal temperature below 0° C. The cooling bath was removed and the reaction mixture was stirred for 2 h and then poured into a separatory funnel. The layers were separated and the aqueous phase was extracted with ethyl acetate (100 mL). The combined organic layers were washed with 5% aqueous citric acid (100 mL), 10% aqueous $NaHCO_3$ (100 mL), water (2×100 mL), and brine (100 mL) and then dried, filtered and concentrated in vacuo to afford an orange foam. The crude material was loaded onto a Florisil® column using tetrahydrofuran as the loading solvent and the column was eluted with 30% ethyl acetate/heptane. The fractions containing the desired product were collected and concentrated in vacuo and then recrystallized from ethyl acetate/heptane. The solids were collected and washed with heptane to afford (9.1 g, 52%) of the desired product as an off-white solid. The filtrate was concentrated in vacuo and purified on silica gel using 40% ethyl acetate/heptane as the eluent to afford and additional 2.5 g (14%) of the desired product. Total yield of 4-(4-fluoro-2-methyl-1H-indol-5-yloxy)-5-methylpyrrolo[2,1-f][1,2,4]triazin-6-ol was (11.6 g, 66%).
Reverse phase HPLC: 3.75 min (YMC S5 ODS column 4.6×50 mm, 10–90% aqueous methanol over 4 minutes containing 0.2% phosphoric acid, 4 mumin, monitoring at 220 nm). LC/MS; $(M+H)^+=313.2$

EXAMPLE 2

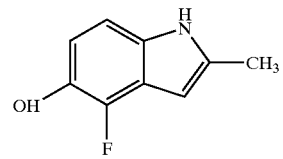

4-Fluoro-2-methyl-1H-indol-5-ol

A. 1-(2,3-Difluoro-6-nitrophenyl)-propan-2-one

A 10 liter reactor was charged with potassium tert-butoxide (570.6 g, 5.082 mol) and tetrahydrofuran (2 L). Overhead stirring was initiated and the resulting suspension was cooled to 11° C. before ethyl acetoacetate (668 mL, 5.082 mol) was added. The addition of the ethyl acetoacetate required 1 h and an exotherm was observed. The rate of addition was controlled so that the internal temperature of the reactor did not exceed 25° C. The resulting mixture became homogeneous and was pale yellow in color. After addition was completed, the reaction mixture was cooled between 10° C. and 15° C. and then 1,2,3-trifluoronitrobenzene (260 mL, 600 g, 2.259 mol) was added dropwise as a solution in tetrahydrofuran (1 L). The addition required 35 min and an exotherm was observed. The rate of addition was controlled so an internal temperature of 21° C. was not exceeded. After addition was complete, the resulting brown reaction mixture was warmed to RT and stirred for 2.5 h, at which time, LC analysis indicated 100% conversion with no trace of 1,2,3-trifluoronitrobenzene remaining. The reaction mixture was recooled to 15° C. and 3 L of 1 N HCl were slowly added over 15 min and the brown solution eventually became a clear yellow solution. The pH of the aqueous phase was ~pH 4. The mixture was extracted with ethyl acetate (2×1 L) and the combined organic extracts were washed with brine (1 L) and concentrated in vacuo to afford an orange oil.

The oil obtained was charged into a 10 L reactor and dissolved in glacial acetic acid (1 L). Sulfuric acid (conc., 1 L) was then added and a vigorous evolution of gas was observed in addition to a slight exotherm. Mechanical stirring was initiated and the reaction mixture was heated at 70° C. for 3 h, after which time LC analysis indicated 100% conversion. The reaction mixture was cooled to between 15° C. to 20° C. and ethyl acetate (3 L) was added followed by the addition of water (6 L). No visible interface was observable. Seven liters of aqueous phase were separated and then extracted with ethyl acetate (2×2 L). At this time, a visible interface was observable. The combined organic extracts were washed with 1 N NaOH (6×1 L) (the pH of the aqueous phase was 6.6) and brine (3×1 L). The brown organic extracts were concentrated under reduced pressure (bath temperature 35° C., 36 torr) for ~10 h to afford 569 g of the desired compound as a crude brown oil which was 82% AP by HPLC.

Residual ethyl acetate was 3% by GC. KF: 0.25%. $^1$H and $^{13}$C NMR matched reported data. Major impurity: para regioisomer.

B. A mixture of 1-(2,3-difluoro-6-nitrophenyl)-propan-2-one (183 g) and potassium carbonate (100 g) in methanol (1 L) was heated at reflux for 3 h. The reaction mixture was then cooled and concentrated in vacuo to remove most of the methanol. The residue was diluted with ethyl acetate (1 L), filtered and washed with water. The separated aqueous layer was neutralized with 2N HCl and extracted with ethyl acetate (2×500 mL). The combined organic layer was washed with brine, dried ($Na_2SO_4$) and concentrated in vacuo to give a brown solid. The solid was triturated with diethyl ether and filtered to provide 1-(2-fluoro-3-methoxy-6-nitrophenyl)-propan-2-one (121 g, 71%) as a yellow solid. LC/MS; $(M+H)^+=228.2$.

C. A mixture of 1-(2-fluoro-3-methoxy-6-nitrophenyl)-propan-2-one from previous step (454 mg, 21 mmol) and pyridinium chloride (0.9 g, 7.8 mmol) was stirred at 180° C. for 75 min. The reaction was cooled to room temperature, diluted with 1N HCl (3 mL) and ethyl acetate (10 mL) and filtered. The filtrate was washed with brine (2×), dried and concentrated in vacuo to give 1-(2-fluoro-3-hydroxy-6nitrophenyl)-propan-2-one (410 mg, 96%) as a grey solid, which was used without further purification for the next step. LC/MS; $(M+H)^+=214$. $^1$HNMR ($CDCl_3$): δ 2.37 (s, 3H), 4.22 (s, 2H), 6.95 (dd, 1H), 7.95 (d, 1H, J=9.35 Hz).

D. 1-(2-fluoro-3-hydroxy-6-nitrophenyl)-propan-2-one from previous step (50 g, 0.234 mol) was added to 2 liter round bottom flask. Water (1 L) was added, and the yellow suspension was stirred at RT. Sodium dithionite (225 g, 5.5 eq) was added in one portion and the reaction mixture was stirred and kept <30° C. until HPLC analysis indicated no starting material remained (typically less than 1 hour). Upon completion, the reaction mixture was cooled to 0° C. and the tan solid product was collected by vacuum filtration. The wet product was dried at <50° C. under house vacuum to afford 4-fluoro-2-methyl-1H-indol-5-ol (31.4 g, 81% yield) which was isolated as a tan crystalline powder. The material had an HPLC purity of >99.8. $^1$H NMR ($CDCl_3$, 400 MHz) δ 7.8 (s, 1H), 6.9–6.7 (m, 2H), 6.2 (s,1H), 4.7 (s, 1H), 2.4 (s, 3H).

$^{13}$C NMR ($CDCl_3$, 100 MHz) δ 145.7, 143.4, 137.5, 136.7, 134.4, 120.1, 112.7, 106.8, 95.4, 13.3.

Also, 1-(2,3-difluoro-6-nitrophenyl)-propan-2-one could be converted to the title compound by an alternate route as described below.

E. 1-(3-Benzyloxy-2-fluoro-6-nitro-phenyl)-propan-2-one

To a solution of 1-(2,3-difluoro-6-nitrophenyl)-propan-2-one (2.5 g, 82% purity by HPLC analysis, 9.54 mmol) were added benzyl alcohol (2.5 mL) and $LiOH.H_2O$ (1.07 g, 25.58 mmol). The reaction mixture was then heated to 100–110° C. and stirred for 4 hours until HPLC analysis indicated complete reaction. After cooling to RT, the reaction mixture was diluted with dichloromethane (18 mL) and neutralized to pH 6–7 with 1 N HCl. The layers were separated and the organic phase was washed with brine and collected. With stirring, heptane (30–25 mL) was added to the organic solution whereupon crystallization was initiated. The resulting slurry was cooled to 0–5° C. and stirred for an additional 1 h. The slurry was then filtered and the filter cake was washed with heptane. The yellow-brown solids were then dried in vacuo at 50° C. for 12–15 h to afford of the desired compound (1.6 g) which was 95% pure by HPLC analysis. HPLC method: Column: YMC Pack Cyano 3 μm, 4.6×50 mm Solvent A: 0.05% TFA in MeOH:Water (20:80), Solvent B: 0.05% TFA in MeOH:water (20:80), Wavelength: 254 nm Flow Rate: 3 mL/min. Gradient Time: 3 min. Final % B: 100 Initial Hold: 0.5 min. Start % B: 0. Typical Retention Times: SM, 1.2 min; Product 2.2–2.3 min.

F. 4-Fluoro-2-methyl-1H-indol-5-ol

To a solution of compound E from previous step (20.00 g, 66.03.30 mmol) in methanol under a nitrogen atmosphere (300 mL) at room temperature in the absence of light were added 10% Pd/C (2.0 g) and ammonium formate (60.0 g, 0.95 mol). The reaction mixture was stirred for 3.5 h and then diluted with ethyl acetate (200 mL) and filtered through a Celite®/silica gel pad. The residue can then be purified by either of the following methods:

After concentration in vacuo, the resulting residue was purified by chromatography eluting with 30% ethyl acetateihexanes to afford (7.32 g, 67%) of the desired compound as a white solid after trituration with dichloromethane/hexanes. After concentration in vacuo, the residue was dissolved in dichloromethane and passed through a silica gel pad washing with dichloromethane. The filtrate was concentrated in vacuo to afford (6.66 g, 61%) of the title compound as a white solid.

Compound E of this example can also be converted to 1-(2-fluoro-3-hydroxy-6-nitrophenyl)-propan-2-one by the following two alternate methods.

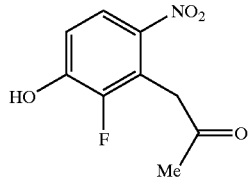

1-(2-fluoro-3-hydroxy-6-nitrophenyl)-propan-2-one
Method G-1: To a solution of 1-(3-benzyloxy-2-fluoro-6-nitrophenyl)-propan-2-one (3.03 g, 10 mmol) in acetic anhydride (5 mL) and acetic acid (5 mL) at room temperature was added hydrobromic acid (48% aqueous solution, 3 mL). After addition, the reaction was heated at 100° C. for 30 min and then cooled to room temperature. To this mixture was added 10 mL of hexanes with stirring. The solution was decanted and concentrated. The residue was diluted with ethyl acetate (50 mL) and washed with brine (3×20 mL). The organic layer was dried and concentrated in vacuo to provide 1-(2-fluoro-3-hydroxy-6-nitrophenyl)-propan-2-one (1.7 g, 80%) as a brown solid, which was used in the next step without further purification. LC/MS; (M+H)$^+$=213.2
Method G-2: A mixture of 1-(3-benzyloxy-2-fluoro-6-nitrophenyl)-propan-2-one (65.0 g, 0.214 mol) and pyridinium chloride (60.74 g, 0.526 mol) was stirred at 180° C. for 1 hr. The reaction mixture was cooled to room temperature, diluted with 3N HCl (100 mL) and ethyl acetate (500 mL) and filtered. The aqueous layer was extracted with ethyl acetate (2×) and the combined organic layers were washed with brine, dried (MgSO$_4$),s filtered through a pad of silica gel and concentrated in vacuo. The residue was decolorized with charcoal in methanol, filtered and concentrated in vacuo to afford 1-(2-fluoro-3-hydroxy-6-nitrophenyl)-propan-2-one (37 g, 81%) as a brown solid. LC/MS; (M+H)$^+$=213.2

Alternatively, 1-(3-benzyloxy-2-fluoro-6-nitrophenyl)-propan-2-one can be cyclized to 5-benzyloxy-4-fluoro-2-methyl-1H-indole as described below, which then can be debenzylated as described before.
H. A mixture of 1-(3-benzyloxy-2-fluoro-6-nitrophenyl)-propan-2-one (9.09 g, 30 mmol) and Raney nickel (~5 g) in methanol (100 mL) was heated to 40° C. and then a solution of hydrazine in methanol (15 mL) was added dropwise with vigorous stirring over a period of 30 min. After refluxing for 1 h, the reaction mixture was cooled to room temperature, filtered through Celite and concentrated. The crude material was passed through a pad of silica gel eluting with dichloromethane and concentrated in vacuo to provide 5-benzyloxy-4-fluoro-2-methyl-1H-indole (6.1 g, 80%) as a yellowish oil. LC/MS; (M+H)$^+$=256.3$^+$.

What is claimed is:
1. A process for preparing a compound of the formula

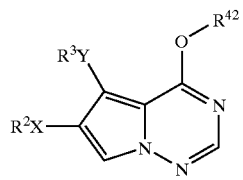

(I)

wherein
X and Y are independently selected from O, or X or Y are absent;

$R^2$ and $R^3$ are independently hydrogen, alkyl or substituted alkyl, $R^{42}$ is

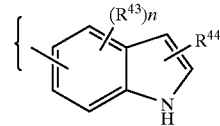

$(R^{43})_n$ wherein n equals 0, 1 or 2 and each $R^{43}$ is independently selected from the group consisting of hydrogen, fluorine, chlorine and methyl; and $R^{44}$ is methyl, or hydrogen, or an enantiomer, diastereomer, or pharmaceutically acceptable salt thereof, which comprises the steps of
a) converting a compound of the formula

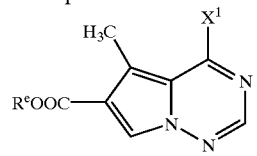

where $R^8$ is lower alkyl or aryl and $X^1$ is a halogen to compound 1 of the formula

1

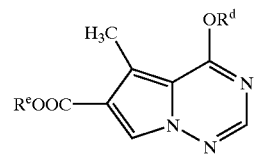

where $R^d$ is lower alkyl, aryl, substituted aryl, heteroaryl or substituted heteroaryl, by treatment with a phenoxide or alkoxide, b) alkylating Compound 1 with an alkylmagnesium bromide to afford Compound 2 of the formula

2

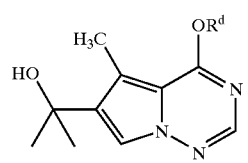

c) treating compound 2 with a peroxide in the presence of a Lewis acid to afford compound 3 of the formula

3

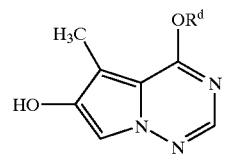

d) alkylating the —OH group in compound 3 to afford Compound 4 of the formula

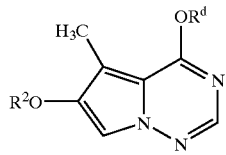
4 where R² is benzyl or substituted benzyl, e) hydrolyzing Compound 4 to afford Compound 5 of the formula

5 where R² is benzyl or substituted benzyl, and f) converting Compound 5 to Compound 6 of the formula

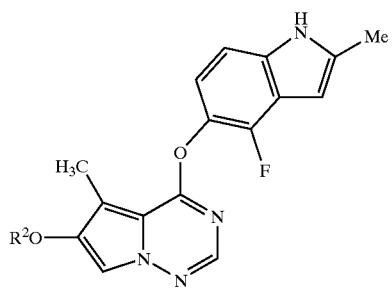
6 by first converting compound 5 to a chloroimidate, subsequently alkylating the chloroimidate with Compound 14 of the formula

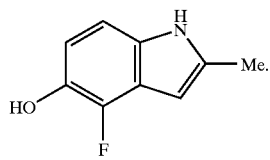
14 to afford Compound 6 wherein R² is benzyl, and deprotecting the phenol by treatment with a hydrogen donor in the presence of a catalyst to afford compound 6 where R² is hydrogen.

2. The process according to claim 1 wherein in step c), hydrogen peroxide is used in the presence of a Lewis acid to convert Compound 2 to Compound 3.

3. A process for preparing a compound of the formula

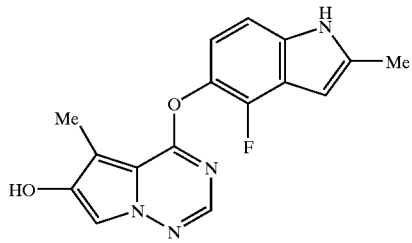
10 which comprises the steps of a) reacting compound 7 of the formula

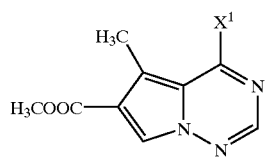
7 where $X_1$ is halogen;

with Compound 14 to afford Compound 8 of the formula

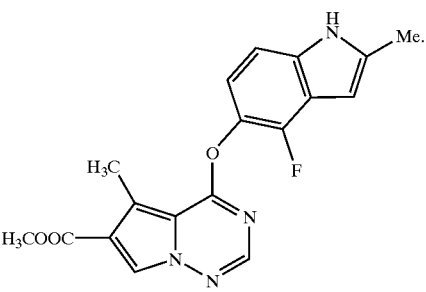
8 b) treating Compound 8 with an alkylating agent at low temperature, to afford Compound 9 of the formula

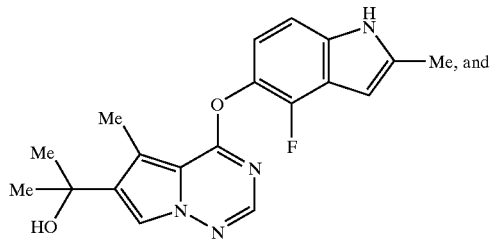
9 c) treating Compound 9 with a peroxide in the presence of a Lewis acid to afford Compound 10 of the formula

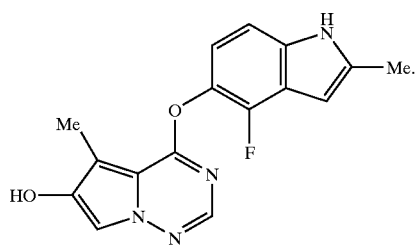
10

4. The process according to claim 3 wherein the alkylating agent in step (b) is an alkyl magnesium halide.

5. The process according to claim 4 wherein the alkyl magnesium halide is methyl magnesium bromide or methyl magnesium chloride.

6. The process according to claim 4 wherein the peroxide used in step c) is hydrogen peroxide or sodium perborate.

7. The process according to claim 4 wherein the Lewis acid used in step c) is boron trifluoride.

8. A process for preparing a compound of the formula

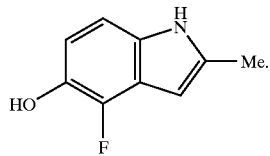
14 which comprises the steps of a) reacting a fluorinated compound of the formula

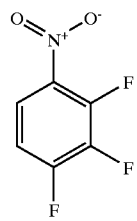

b) with an alkyl acetoacetate to afford Compound 11 of the formula

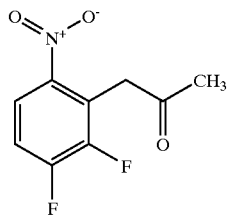
11 c) reacting Compound 11 with an alkoxy anion to afford Compound 12 of the formula

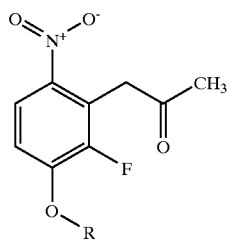
12 wherein R is a protecting group, d) deprotecting the alkoxy group by treatment with a deprotecting reagent to afford Compound 13 of the formula

13

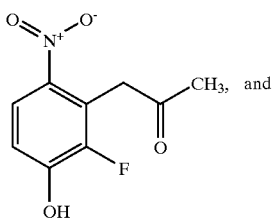 and e) cyclizing Compound 13 under reducing conditions to afford Compound 14.

14

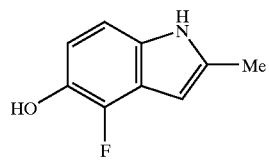

9. The process according to claim 8 wherein the reduction in step (e) utilizes sodium dithionite in water or a mixture of water and an organic solvent such as THF.

10. The process according to claim 8 wherein the reduction in step (d) utilizes pyridinium chloride or pyridinium iodide or hydrogen bromide.

* * * * *

UNITED STATES PATENT AND TRADEMARK OFFICE
CERTIFICATE OF CORRECTION

PATENT NO. : 6,933,386 B2
DATED : August 23, 2005
INVENTOR(S) : Bhide et al.

It is certified that error appears in the above-identified patent and that said Letters Patent is hereby corrected as shown below:

Column 26,
Line 32, should read -- where $R^e$ is lower alkly or aryl and $X^1$ is a halogen to compound 1 of the formula --.

Column 28,
Line 33, structure 9 should read:

-- 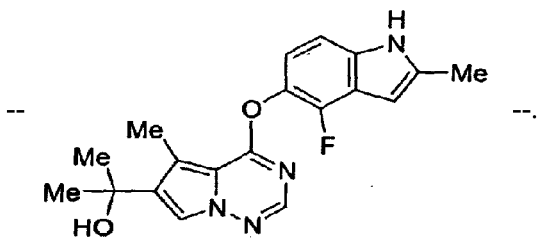 --.

Column 30,
Line 20, structure 13 should read:

-- 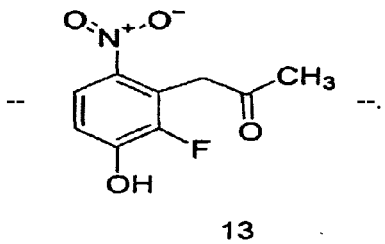 --.

Signed and Sealed this

Sixteenth Day of May, 2006

JON W. DUDAS
*Director of the United States Patent and Trademark Office*